United States Patent [19]

Shillington et al.

[11] Patent Number: 5,103,997
[45] Date of Patent: Apr. 14, 1992

[54] COMBINATION DISPOSABLE SHARPS CONTAINER AND MOUNTING BRACKET

[75] Inventors: Richard A. Shillington, Leucadia; Robert D. Miller, Costa Mesa; Rex O. Bare, Lake Forest, all of Calif.

[73] Assignee: Med-Safe Systems, Inc., Carlshad, Calif.

[21] Appl. No.: 617,897

[22] Filed: Nov. 26, 1990

Related U.S. Application Data

[63] Continuation-in-part of Ser. No. 446,121, Dec. 12, 1989.

[51] Int. Cl.⁵ .............................................. B65D 25/22
[52] U.S. Cl. ................................. 220/481; 220/94 R; 206/366; 206/370; 248/221.4; 248/225.1
[58] Field of Search .................. 206/365, 366, 370; 220/908, 480, 910, 481, 630, 85 H, 252, 335; 248/221.3, 221.4, 223.4, 225.1

[56] References Cited

U.S. PATENT DOCUMENTS

| | | | |
|---|---|---|---|
| 546,706 | 9/1895 | McConnelll | 220/481 |
| 2,754,991 | 7/1956 | Hagerty et al. | 220/481 |
| 3,078,484 | 2/1963 | Briggs | 248/223.4 |
| 3,915,189 | 10/1975 | Holbrook et al. | 248/223.4 |
| 4,577,563 | 3/1986 | Sidler | 220/481 |
| 4,702,385 | 10/1987 | Shillinygton | 220/481 |
| 4,736,860 | 4/1988 | Bemis | 220/481 |
| 4,850,484 | 7/1989 | Denman | 220/480 |
| 4,915,336 | 4/1990 | Handy | 248/221.3 |
| 4,930,653 | 6/1990 | Machado | 220/630 |
| 4,955,477 | 9/1990 | Bruno | 206/366 |

FOREIGN PATENT DOCUMENTS

| | | | |
|---|---|---|---|
| 7707911 | 7/1977 | Fed. Rep. of Germany | 248/221.4 |
| 2300290 | 10/1976 | France | 248/221.3 |
| 1303645 | 1/1973 | United Kingdom | 220/481 |
| 2047519 | 12/1980 | United Kingdom | 248/223.4 |

*Primary Examiner*—Stephen Marcus
*Assistant Examiner*—S. Castellano
*Attorney, Agent, or Firm*—Baker, Maxham, Jester & Meador

[57] ABSTRACT

A combination of a secure disposable container and mounting bracket assembly therefor, comprises a generally box-like enclosed container having a top with a limited access closure for receiving medical sharps and for inhibiting access by a human hand, the container having a back wall with a downwardly extending latching slot at an upper edge thereof, and a latching tab at a lower edge thereof, a generally rectangular panel having a back mounting surface and mounting holes for mounting the panel to a vertical support surface, and mounting tabs for mounting the panel to another mounting bracket mounted on a vertical supporting surface, an upper edge for receiving the downwardly extending latching slot on the container, a lower transverse ledge, and lever operated can for camming the tab on the lower edge of the container into gripping engagement with the lower transverse ledge.

19 Claims, 3 Drawing Sheets

COMBINATION DISPOSABLE SHARPS CONTAINER AND MOUNTING BRACKET

REFERENCE TO RELATED APPLICATIONS

The present application is a continuation-in-part of application Ser. No. 07/446,121, filed Dec. 12, 1989, and entitled "A Secure Container for Disposable Sharps".

BACKGROUND OF THE INVENTION

The present invention relates to disposable containers for hospital sharps and waste, and pertains particularly to a secure mounting assembly and secure disposable container for disposition of hospital sharps, objects and wastes.

Hospitals and medical clinics use great quantities of sharps, such as needles, syringes, surgical blades, and the like, that are disposed of rather than cleaned and reused. It is necessary that the sharps be disposed of in a manner that prevents them being reused without sterilization. In particular, it is necessary to keep them from falling into the hands of those, such as intravenous drug users and the like, who are likely to use them without proper sterilization.

Numerous containers have been developed in recent years, which are reasonably secure and disposable for receiving and disposing of hospital sharps, wastes and the like. Many of these disposable containers, however, are out dated and do not provide adequate security against pilfering of used syringes and the like from such containers. While improved containers have been developed which cannot readily be reopened and articles cannot be easily removed therefrom, such containers must be kept in a secure place or securely mounted to non-removable structure to prevent unauthorized removal. The disposable container and its mounting bracket must not only be secure, it must be simple and inexpensive to manufacture, and it must be simple and easy to use and to mount and remove the container.

Reasonably secure mounting brackets have been developed and widely used in the past to prevent unauthorized removal of the containers. However, recently developed improved containers also have new and improved mounting brackets which are easier to use and are more secure. These older brackets are typically mounted on walls or similar surfaces and are securely anchored by lag bolts and the like. The removal of the old bracket and the installation of a new bracket requires the services of skilled workman with special tools, with which the hospitals and clinics do not wish to bother. This frequently results in resistance by hospitals and clinics to new and improved disposable containers that require a different bracket.

An example of a prior art container and mounting bracket is disclosed in U.S. Pat. No. 4,736,860 of Bemis dated Apr. 12, 1988. This patent discloses a sharps container having a door that provides limited access to the interior of the container, and having a mounting bracket adapted to be mounted to a wall with inter-engaging projections and slots on the bracket and container for securing the container to the bracket. A special tool is required to disengage the container from the bracket.

It is, therefore, desirable that an improved securable disposable container and bracket assembly be available which does not require removal of the old bracket.

SUMMARY AND OBJECTS OF THE INVENTION

It is the primary object of the present invention to provide an improved securable disposable container and bracket assembly.

In accordance with a primary aspect of the present invention, a secure disposable container assembly comprises a housing for securely and detachably mounting to a support member, and having an access opening in a top front for receiving a disposable article and preventing access to the interior of the container by the human hand. Means are provided for locking the housing to a support bracket to prevent removal of the container.

BRIEF DESCRIPTION OF THE DRAWING

The above and other objects and advantages of the present invention will become apparent from the following description when read in conjunction with the accompanying drawings wherein.

DETAILED DESCRIPTION OF A PREFERRED EMBODIMENT

Figure 1:
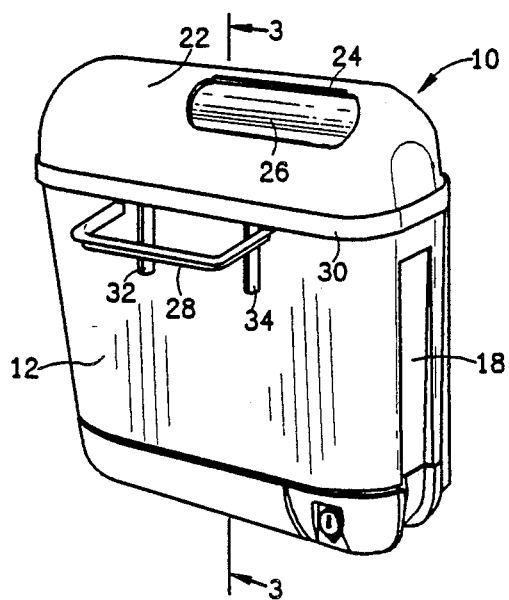
FIG. 1 is a perspective view of an exemplary embodiment of the invention.

Referring to FIG. 1 of the drawing, there is illustrated an exemplary embodiment of a disposable sharps container assembly in accordance with the invention, designated generally by the numeral 10. The container comprises a generally rectangular box-like housing, formed of the usual plastic material for such containers, and detachably mounted to a wall bracket. The housing in its preferred form is formed of a lower substantially rectangular shell, having a front wall or panel 12 and a back wall or panel 14 (FIGS. 3 and 4) defining front and back walls, and further including opposed side walls 16 and 18. These walls are formed integral with and extend upward from a generally rectangular bottom panel 20 terminating at a top rectangular peripheral edge and downturned rim or skirt 30. A generally semi-circular top shell 22 is secured to the top peripheral edge 30 of the rectangular shell 10.

The top cover 22 and bottom shell or housing may be molded together with a live hinge or they be molded separately and utilize snap lock tabs or hinges (not shown). A live hinge is a thin strip of the housing material connecting the two members and allowing them to pivot relative to one another. The top cover 22 and the bottom shell may be secured together in any number of ways, such as disclosed in the parent application or in a companion application to be filed concurrently herewith.

The container top cover and bottom shell are preferably injection molded of a suitable plastic, and preferably formed with a slight taper from top to bottom to enable stacking for ease of shipment. The top 22 cover has a generally semi-cylindrical configuration about a horizontal axis, about which a pivoting closure member is mounted, as more fully disclosed in the parent application. Referring to FIG. 1, the top cover 22 is provided with a top front opening 24 of a generally elongated configuration having circular or oval ends. This opening 24 is formed in the upper front one side of the top 22 extending approximately one-half the length of the top. This opening is designed to receive syringes and the like for disposal and to secure the syringes against unauthorized retrieval.

The opening 24 is closed by a pivoting closure member 26 (FIG. 3), as more fully disclosed in the parent application and the companion application. The closure member 26 has a generally horizontal receiving surface or ledge portion disposed below the opening 24 for receiving syringes, and a face portion extending upward at approximately a forty-five degree angle to an upper curved closure portion. These faces together form a combination closure and receiving support for disposable articles, such as a syringe or the like. When a syringe or the like is inserted into the opening and placed on the receiving surface of the closure, the closure rotates under the weight of the syringe and dumps it.

The container is designed for ease of handling and to this end is provided with a retractable handle 28 that is preferably molded integrally with the lower edge of a peripheral rim or skirt 30. The handle 28 is pivotal outwardly, as shown for ease of grasping, and downward to a retracted position, engaging and latching to the lower ends of detent bars 32 and 34.

Figure 2:
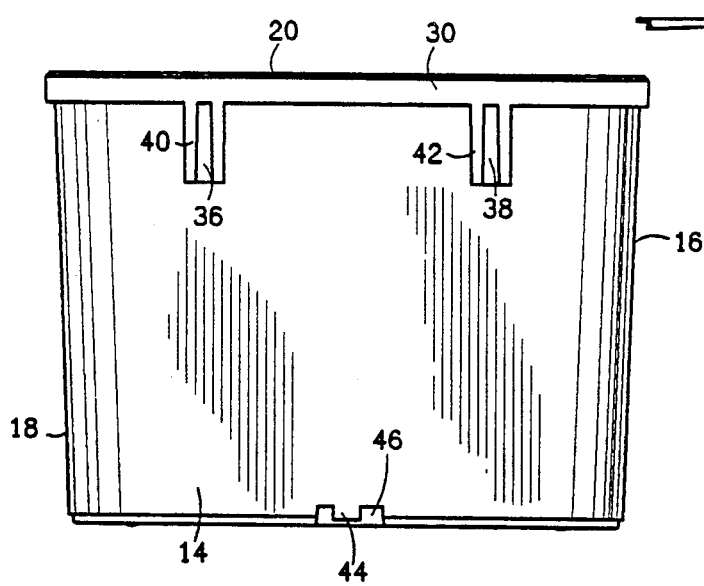
FIG. 2 is a rear view of the container showing details of the mounting components of the container.
Figure 3:
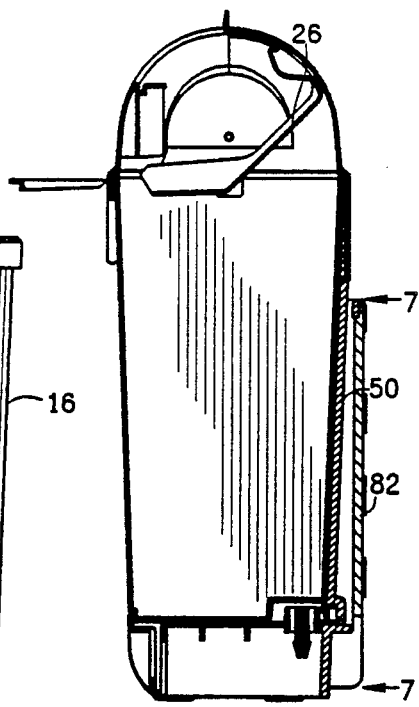
FIG. 3 is a section view taken on line 3—3 of FIG. 3.

Referring to FIGS. 2 and 3, the back of the container is provided with means for attachment to a wall bracket to be described. The attachment means comprises a pair of hook slots 36 and 38 extending downwardly from the top back of the container. These slots are formed in an outer or outwardly spaced wall 40 and 42 of downwardly extending sockets formed on the back wall 14 of the container. The slots extend and hook over a pair of side walls, only one 56a shown, as will be explained.

A latching tab 44 at the lower end of the back wall 14 extends downward and is biased by a cam or lever outwardly at about 90 degrees into latching engagement with a shoulder on and at the lower edge of the wall mount for latching the container in place to the wall mount. The tab 44 extends down at the outer edge of a cavity or recess 46 in the bottom back edge of the container.

Figure 4:
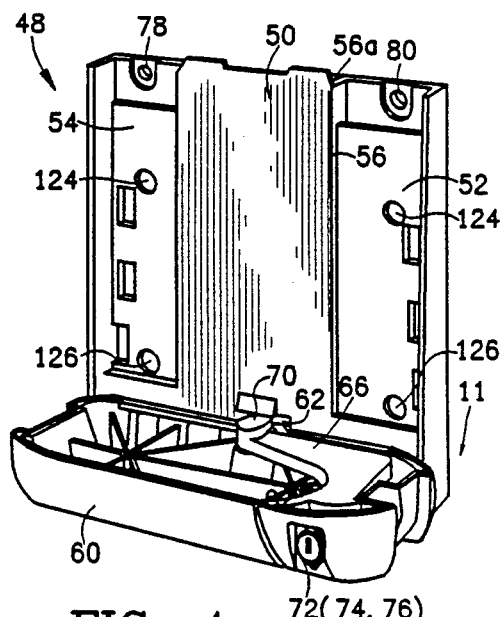
FIG. 4 is a perspective view of the mounting bracket of the embodiment of FIG. 1.
Figure 8:
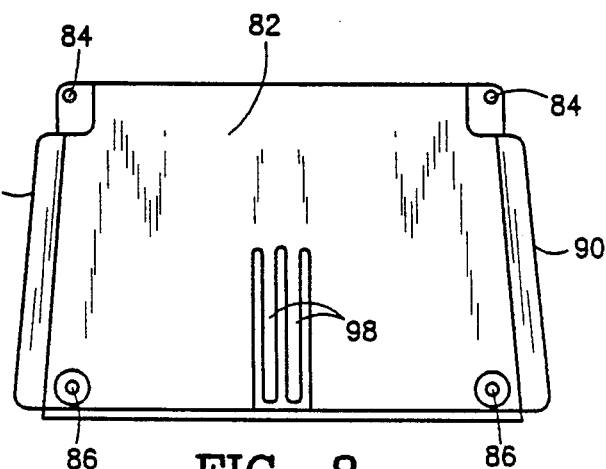
FIG. 8 is a front elevation view of a prior art bracket.

A wall mounting bracket is illustrated in FIG. 4, designated generally by the numeral 48, and is constructed to mount either to a vertical support surface or to a previously mounted bracket (FIG. 8). The mounting bracket comprises a generally rectangular vertical panel comprising a generally planar central panel 50 secured to and extending upwardly from a latching housing 60 to be described. The vertical panel comprises central panel 50 and forwardly stepped side panels 52 and 54 connected by forwardly extending side walls 56 and 58. The central panel 50 has an upper edge 50a which extends beneath the skirt 30 on the back of the container between slots 36 and 38. The forwardly extending walls 56 and 58 have upper edges 56a and 58a which extend into and along slots 36 and 38 of the container. This arrangement of upper wall edges engages and supports the upper end of the container.

Figure 9:
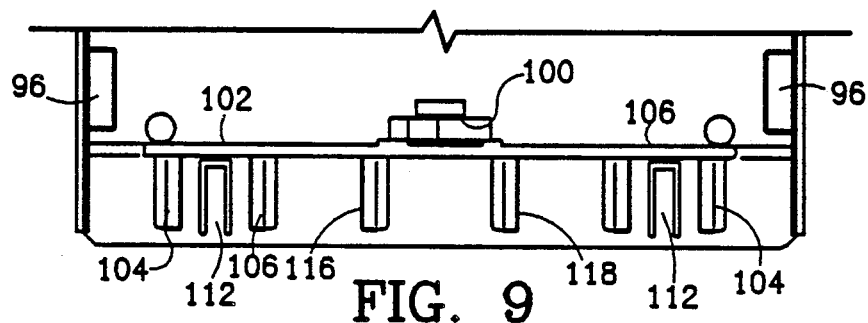
FIG. 9 is an enlarged detailed view of a lower part of the mounting bracket.
Figure 10:
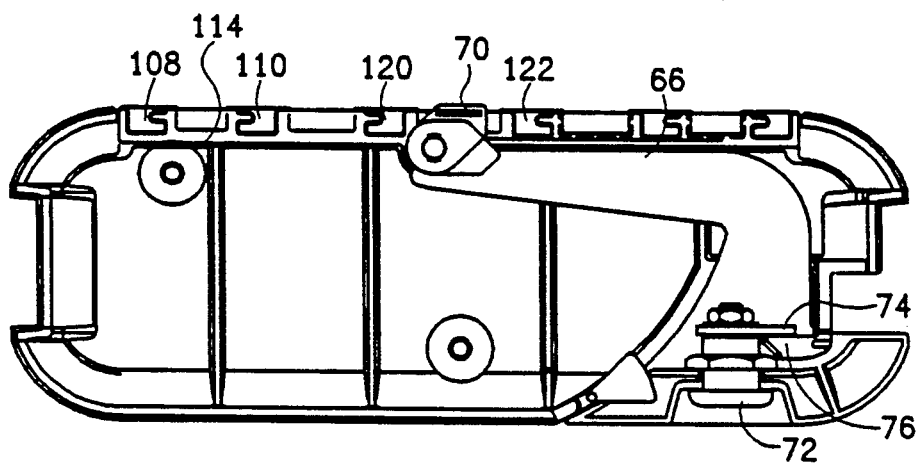
FIG. 10 is a top plan view of the bracket housing.
Figure 11:
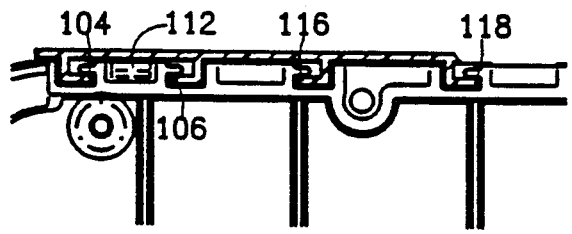
FIG. 11 is a view taken generally on line 9—9 of FIG. 7.

A lower housing 60 is permanently attached to or made integral with the vertical panel and houses the latching and locking mechanism. The panel 50 and the housing 60 are preferably made separately, such as by molding and latched together by snap-fit latching means, as shown in FIGS. 9-11. The housing 60 is sized and shaped to form the appearance of an extension of the container and to cover the lower end thereof. The face of panel 50 facing the housing 60 is considered the front face of the panel for purposes herein.

Figure 6:
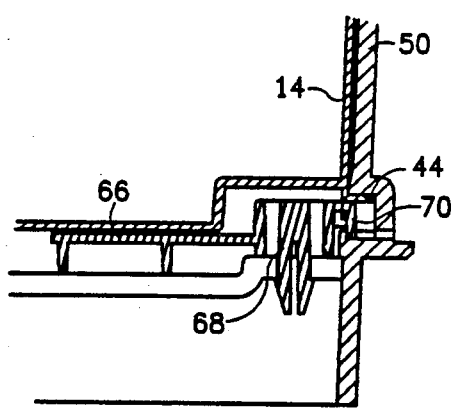
FIG. 6 is a view like FIG. 5 showing the apparatus in the latched position.
Figure 5:
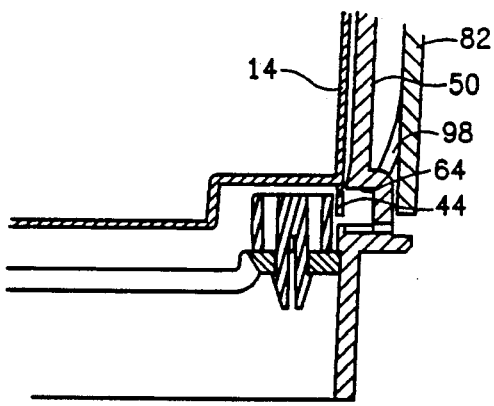
FIG. 5 is a detailed partial view of the latching apparatus for the container shown in the unlatched condition.

As best shown in FIGS. 5 and 6, a latch recess 62 forms a shoulder or ledge 64 on the lower front of panel 50 and includes a horizontal extending shoulder or gripping ledge 64 against which tab 44 is biased for latching the container in place on the mounting bracket. The latch shoulder 64 is preferably formed as an upper edge of a recess 62 formed in the lower portion of the panel 50.

A latching lever or arm 66 (FIG. 1) is pivotally mounted in the housing 60 by a shaft 68 and includes a latching cam or finger 70 on the inner end. The latching cam or finger engages tab 44 and biases it under and into engagement with latch surface 64 for latching the container in place.

The outer end of the arm 66 includes a lock assembly, including a rotatable shaft 72 with an arm 74 that extends behind a shoulder 76 and locks the lever 66 in the inner position. When the lever 66 is pivoted outward, cam or finger 70 is pulled away from shoulder 64, and the tab 44 is released so that the container may be lifted upward and removed from the mounting bracket. The lock assembly 72 is of conventional construction, having a key slot for receiving a key to rotate a shaft 72 having a finger or arm 74, which in one position engages a shoulder 76 in housing 60 for locking the arm in the inner position.

The mounting bracket 48 may be mounted to a vertical support surface, such as a wall by screws or lag bolts extending through mounting holes 78 and 80. It may also preferably be constructed to mount onto other mounting brackets. An exemplary embodiment of a typical wedge type bracket is illustrated in FIG. 8, and includes a panel 82 having upper mounting holes 84 and lower mounting holes 86 for attachment by bolts or screws to a wall or the like. The panel includes a pair of non-parallel sides 88 and 90 forming opposed downwardly diverging mounting rails for receiving a disposable container or the like.

Figure 7:
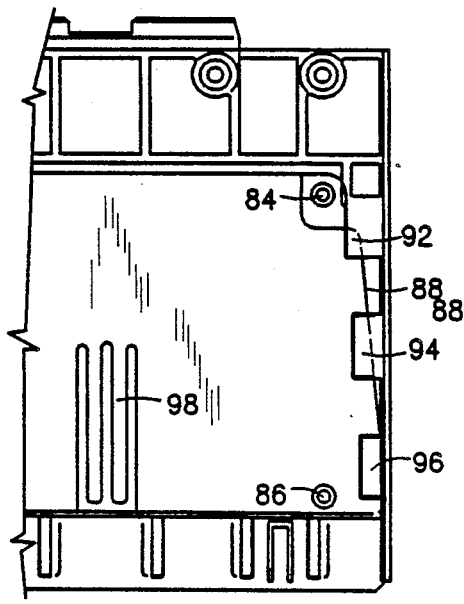
FIG. 7 is a partial back elevation view taken generally on line 7—7 of FIG. 3.

The panel of applicant's bracket, as illustrated in FIG. 7, includes a plurality of opposed fingers or tabs 92, 96, and 98 which extend outward from the back of the panel 50, around and engage the side rails 88 and 90 for mounting applicant's bracket onto the prior art bracket 82. These fingers are stepped out or diverge downward, as seen in FIG. 7, to cooperative with diverging rails 88 and 90. A pair of fingers 98 on the prior art bracket 82 engages a ledge 100 on the back face of applicant's panel for locking the applicant's bracket in place on the prior art bracket (FIG. 5). This essentially permanently locks the applicant's bracket to the prior art bracket. The applicant's bracket is provided with holes for access to mounting screws of the prior art bracket.

Referring FIGS. 9 and 10, the snap in connection between the back panel and lower housing of the wall bracket is best illustrated. Referring first to FIG. 9, the container side of the back panel is illustrated and has a lower portion which extends below a horizontal bar or shoulder 102. This lower portion is adapted to extend and latch into a back recess or socket portion of the lower housing 60 (FIG. 11). A latch assembly on each side of the bracket includes a pair of guide rails 104 and 106 on the lower panel, which engage L-shaped guide notches 108 and 110 on the lower housing (FIG. 10) to guide and hold the panel in position. A latch tab 112 between the rails 104 and 106 engage a shoulder 114 on the housing 60 and latch the panel and housing together. A center guide assembly includes similar rails 116 and 118 which engage guide slots 120 and 122. When the panel and the lower housing is secured together, the tabs 112 are inaccessible and the housing and panel become non-removably locked together.

In normal operation, to dispose of a syringe as viewed in FIG. 1, the syringe is inserted into the top opening, with the needle extending toward the left to extend inside and underneath the top of the housing, such that the body of the syringe is placed on the horizontal closure surface (not shown). The weight of the syringe overcomes the counterweight of the closure and tilts the closure member to dump the syringe into the container. As soon as the container is filled, the container is removed and another container is mounted on the wall bracket.

Removal of the container is accomplished by inserting a key in the lock 72 and rotating the key until the lock is released. The key and lever 66 is then pulled outward to pivot the lever and release the tab 44 on the container from engagement by cam or finger 70. The container is then lifted upwardly, such by handle 28 releasing the slots from engagement with the upper back of the bracket panel. The container is then removed and a new container installed by reversal of the above procedure.

The mounting bracket 48 is preferably provided with upper holes 124 and lower holes 126 aligned with mounting holes 84 and 86 on mounting bracket 82 to enable access to screws or the like therein. This enables the bracket to be removed from a wall.

While we have illustrated and described our invention by means of specific embodiments, it is to be understood that numerous changes and modifications may be made therein without departing from the spirit and scope of the invention as defined in the appended claims.

We claim:

1. A combination secure sharps disposal container and mounting bracket assembly therefor, comprising:
   a generally box-like enclosed container having a top with a limited access closure for receiving medical sharps and inhibiting access by a human hand;
   a mounting bracket for mounting said container to a supporting structure comprising a generally rectangular panel having a top and a bottom and first attaching means for attachment to a vertical support structure;
   first latching means at said top for latching engagement with an upper edge of said container; and
   second latching means at a lower edge of said panel comprising a horizontally extending ledge, and means for biasing a tab at a lower edge of said container into latching engagement with said ledge, said second latching means comprises a lever mounted for pivoting toward and away from said panel, and said means for biasing said tab includes an arm on one end of said lever.

2. A combination according to claim 1 wherein:
   said first latching means comprises an upwardly extending horizontal edge at said top of said panel for engaging a downwardly opening mounting slot on said disposable container.

3. A combination according to claim 2 wherein:
   said panel includes second attaching means for attachment to a second bracket.

4. A combination according to claim 3 wherein:
   said mounting bracket comprise a housing at the bottom of said panel and said lever is pivotally mounted in said housing.

5. A combination according to claim 4 wherein:
   said housing includes locking means for locking said lever in an inner position wherein said tab is biased to said latched position.

6. A combination according to claim 5 wherein:
   said housing and said panel are constructed as separate elements and secured together by latching means at the bottom of said panel that is inaccessible when in the latched position.

7. A combination secure sharps disposal container and mounting bracket assembly therefor, comprising:
   a generally box-like enclosed container having a top with a limited access closure for receiving medical sharps and inhibiting access by a human hand;
   a mounting bracket for mounting said container to a supporting structure comprising a generally rectangular panel having a top and a bottom and first attaching means for attachment to a vertical support structure;
   first latching means at said top for latching engagement with an upper edge of said container;
   second latching means at a lower edge of said panel comprising a horizontally extending ledge, and means for biasing a tab at a lower edge of said container into latching engagement with said ledge;
   said mounting bracket comprises a housing at the bottom of said panel; and
   said second latching means comprises a lever mounted in said housing for pivoting toward and away from said panel, and said means for biasing said tab includes an arm on one end of said lever.

8. A combination according to claim 7 wherein:
   said housing includes locking means for locking said lever in an inner position wherein said tab is biased to said latched position.

9. A combination according to claim 8 wherein:
   said housing and said panel are constructed as separate elements and secured together by latching means at the bottom of said panel, said latching means being inaccessible when in the latched position.

10. A combination secure disposable container and mounting bracket assembly therefor, comprising:
    a generally box-like enclosed container having a top with a limited access closure for receiving medical sharps and for inhibiting access by a human hand;
    said container having a back wall with downwardly opening vertically extending latching slot means at an upper edge thereof, and a downwardly depending latching tab at a lower edge thereof;
    a mounting bracket comprising a generally rectangular panel having a back mounting surface and means for mounting said panel to a vertical support surface;

an upper upwardly directed transverse edge for extending into said downwardly opening vertically extending latching slot on said container;

a lower transverse ledge on said panel; and lever operated latching finger for latching engagement with said tab on said lower edge of said container and said lower transverse ledge.

11. A combination according to claim 10 wherein:

said mounting panel includes second mounting means for mounting said panel on a second mounting bracket.

12. A combination according to claim 11 wherein:

said second mounting means comprises fingers spaced outward from the back of said mounting panel for engaging diverging side rails of a wedge type mounting bracket.

13. A combination according to claim 12 wherein:

said mounting bracket comprises a housing at the bottom of said panel and said lever is pivotally mounted in said housing; and said housing includes locking means for locking said lever in an inner position wherein said tab is biased to said latched position.

14. A combination according to claim 13 wherein:

said downwardly extending latching slot means comprises a downwardly turned lip at an upper edge of said container.

15. A combination according to claim 14 wherein:

said downwardly extending latching slot means comprises a pair of laterally spaced forwardly extending wall members having a vertically extending slot therein for receiving an upper edge of a pair of forwardly extending walls of said panel.

16. A combination according to claim 15 wherein:

said pivotable closure includes locking tabs for engaging slots in said top adjacent said access opening for permanently locking said closure in a close position.

17. A combination secure disposable container and mounting bracket assembly therefor, comprising:

a generally box-like enclosed container having a top with a limited access closure for receiving medical sharps and for inhibiting access by a human hand;

said container having a back wall with downwardly opening vertically extending latching slot means at an upper edge thereof, and a downwardly extending latching tab at a lower edge thereof;

a mounting bracket comprising a generally rectangular panel having a back mounting surface and first mounting means for mounting said panel to a vertical support surface, and second mounting means for mounting said panel to a face of a wedge type panel mounting bracket mounted on a vertical supporting surface;

an upper vertically directed transverse edge on said panel for extending into said downwardly opening latching slot on said container;

a lower transverse ledge at a front bottom portion of said panel;

lever operated finger for latching engagement with said tab on said lower edge of said container and said lower transverse ledge;

a housing at the bottom of said panel and said lever is pivotally mounted in said housing; and said housing includes locking means for locking said lever in an inner position wherein said finger is biased to said latched position.

18. A combination according to claim 17 wherein:

said second mounting means comprises fingers spaced outward from the back of said mounting panel for engaging diverging side rails of a wedge type mounting bracket.

19. A combination according to claim 18 wherein:

said housing and said panel are constructed as separate elements and secured together by latching means at the bottom of said panel, said latching means being inaccessible when in the latched position.

* * * * *